(12) United States Patent
Ivanov et al.

(10) Patent No.: US 9,856,205 B2
(45) Date of Patent: Jan. 2, 2018

(54) METHOD FOR THE SELECTIVE PRODUCTION OF N-METHYL-PARA-ANISIDINE

(75) Inventors: Yuriy Alexandrovich Ivanov, Moscow (RU); Alexander Yurievich Frolov, legal representative, Moscow (RU); Nikolay Grigorievich Beliakov, Moscow (RU)

(73) Assignee: IFOTOP LIMITED LIABILITY COMPANY, Moscow (RU)

( * ) Notice: Subject to any disclaimer, the term of this patent is extended or adjusted under 35 U.S.C. 154(b) by 137 days.

(21) Appl. No.: 14/348,262

(22) PCT Filed: Nov. 15, 2011

(86) PCT No.: PCT/RU2011/000901
§ 371 (c)(1),
(2), (4) Date: Feb. 19, 2015

(87) PCT Pub. No.: WO2013/048279
PCT Pub. Date: Apr. 4, 2013

(65) Prior Publication Data
US 2015/0175525 A1 Jun. 25, 2015

(30) Foreign Application Priority Data
Sep. 28, 2011 (RU) ................. 2011139487

(51) Int. Cl.
*C07C 213/08* (2006.01)
*C07C 213/02* (2006.01)
*B01J 23/80* (2006.01)
*B01J 23/86* (2006.01)
*B01J 23/889* (2006.01)
*B01J 25/02* (2006.01)
*C07C 213/00* (2006.01)

(52) U.S. Cl.
CPC ............. *C07C 213/08* (2013.01); *B01J 23/80* (2013.01); *B01J 23/868* (2013.01); *B01J 23/8892* (2013.01); *B01J 25/02* (2013.01); *C07C 213/00* (2013.01); *C07C 213/02* (2013.01)

(58) Field of Classification Search
None
See application file for complete search history.

(56) References Cited

FOREIGN PATENT DOCUMENTS

| RU | 2207335 | 6/2003 |
| RU | 2309944 | 11/2007 |
| SU | 166036 | 11/1964 |

OTHER PUBLICATIONS

RU2263107 Derwent Abstract 2005, pp. 1-3.*
Khimicheskaya entsiklopediya, 1988 "Sovetskaya Entsyklopediya" M., book 1, p. 265, col. 521.
Brown et al., "Mechanism of Aromatic Amine Antiknock Action", Industrial and Engineering Chemistry, 1955, vol. 47, No. 10, pp. 2141-2142.
International Search Report of PCT/RU 2011/000901 dated Jun. 7, 2012.

* cited by examiner

*Primary Examiner* — Clinton Brooks
(74) *Attorney, Agent, or Firm* — BCF LLP

(57) ABSTRACT

The invention "Method for selective synthesis of N-methyl-para-anisidine" relates to chemical technology processes, namely to catalytic alkylation of aromatic amines and nitro compounds.

The invention relates to the method for synthesis of N-methyl-para-anisidine (N-methyl-para-methoxyaniline; N-methyl-para-amino anisole) from para-anisidine (para-amino anisole; para-methoxyaniline) or para-nitro anisole (1-methoxy-4-nitrobenzene) and methanol in the presence of hydrogen or without hydrogen on heterogeneous catalyst. Proposed method permits to use existing process plants used for obtaining aniline and 14-methylaniline.

The invention purpose is to provide the possibility to produce N-methyl-para-anisidine with purity at least 98% and high output that allows arrangement of highly profitable industry-scale manufacturing process.

12 Claims, No Drawings

METHOD FOR THE SELECTIVE PRODUCTION OF N-METHYL-PARA-ANISIDINE

The invention relates to chemical technology processes, namely to catalytic alkylation of aromatic amines and nitrocompounds.

The invention relates to synthesis of N-methyl-para-anisidine (N-methyl-para-methoxyaniline; N-methyl-para-amino anisole) from para-anisidine (para-amino anisole; para-methoxyaniline) or para-nitro anisole (1-methoxy-4-nitrobenzene) and methanol in the presence of hydrogen or without hydrogen on a heterogeneous catalyst.

Proposed method allows to use existing process plants dealt with manufacturing of aniline and 14-methylaniline.

Nowadays, N-methyl-para-anisidine is used as antiknock additive to motor fuel [Pat. 2 309 944, Russian Federation, IPC C07C217/82, C07C235/24, C10L1/223, C10L1/224. Para-methoxyaniline derivatives that increase resistance of hydrocarbon fuel to detonation, and fuel composition (alternatives)/Yu. Ivanov, A. Frolov et al.—No 2006111933/04, filed 12 Apr. 2006, published 10 Nov. 2007, Bul. No 31].

Taking into account unique properties of N-methyl-para-anisidine, which is the simple, complex ether, its application as additives to petrol is quite promising; and it is constrained only by the absence of industrial-scale manufacturing.

In this connection, development of cost-effective industrial method for N-methyl-para-anisidine synthesis is a critical task.

The process for N-methyl-para-anisidine synthesis is known [Pat. 2 309 944, Russian Federation, IPC C07C217/82, C07C235/24, C10L1/223, C10L1/224. Para-methoxyaniline derivatives that increase resistance of hydrocarbon fuel to detonation, and fuel composition (alternatives)/Yu. Ivanov, A. Frolov et al.—No 2006111933/04, filed 12 Apr. 2006, published 10 Nov. 2007, Bul. No 31], which contains reliable evidences that N-methyl-para-anisidine is actually synthesized. Results are given after its physical-chemical and spectral study, which confirm its structure. In this paper two ways of N-methyl-para-anisidine synthesis are described: from N-methyl-N-acetyl-para-anisidine by boiling with sulfuric acid, adding sodium hydroxide and further extraction by toluene as well as using the way described in [Weygand-Hilgetag. Experimental methods in organic chemistry.—Moscow: Chemistry, 1964.—944 p.] using dimethylsulfate, sodium hydrocarbonate, sodium or potassium hydroxide with output 50% from the predicted value. However, this synthesis processes are preparative and not acceptable for N-methyl-para-anisidine synthesis in industrial scale.

Assessment of periodical and patent literature allowed to find the paper describing the process of N-alkyl-para-anisidine synthesis. In the paper [Inventor's certificate 166036 USSR, IPC C07c. Method of producing N-alkyl-P-anisidines/L. Skripko (USSR).—No. 805087/23-4; filed 29 Nov. 1962; published 10 Nov. 1964, Bul. No 21-2c.], the method is proposed for para-anisidine alkylation with aliphatic alcohols. According to it, alkylation was carried out during boiling of the para-anisidine solution in aliphatic alcohol with backflow condenser and using Raney nickel. Process temperature was defined by the boiling temperature of the para-anisidine solution in particular aliphatic alcohol. In this way, N-amyl-para-anisidine, N-decyl-para-anisidine, N-cyclohexyl-para-anisidine was obtained. Target product output was 91.5-98.3% from predictive value.

There are good results; however, one should note that obtained values may be considerably excessive. As a matter of fact, the output of alkylated products was defined in this inventor's certificate upon results of simple catalysate distillation, which does not make an opportunity to isolate pure N-alkylanisidines.

To make an objective method evaluation, there is also lack of the data on the catalyst performance duration (the number experiment repetitions per the same catalyst load); catalyst consumption is unacceptably high without these data.

The main disadvantage of this process, which makes it impossible to use for our purpose, is that the para-anisidine solution in methanol boils at a temperature below 100° C., at which methanol dehydration does not occur and, correspondingly, methylation does not take place.

Lack of information concerning N-methylation of para-anisidine or para-nitroanisole urged us to pay attention to the synthesis of N-alkylated anilines, which have the structure similar to our object, which is described complete enough. At the same time, we understood that nitrogen nucleophilicity in para-anisidine is significantly higher than in aniline and, correspondingly, para-anisidine has the higher reaction capacity to N-alkylation and to N,N-dialkylation. This fact imposes certain limitations to transfer the data obtained during N-alkylation of anilines to N-methylation of para-anisidine or para-nitroanisole. Etheric nature of para-anisidine is the second limitation, which does not permit to use N-alkylation methods resulting in ether hydrolysis.

Taking into account the above limitations, the below data were considered concerning synthesis of N-alkylated amines.

The method is known for the gas-phase aniline alkylation with alcohols on the aluminosilicate catalyst covered by 2-5% of nickel oxide at a temperature 200-250° C. by joint passing of vapors of aniline and alcohol, which is taken in 3-4-fold excess, through the catalyst with further isolation of reaction product. Output of the mixture of mono- and dialkylanilines is 95-98%. Derivatives of isopropyl, isobutyl, butyl, nonyl alcohols were obtained [Inventor's certificate 666167 USSR, C07c 85/06, C07c 87/50, A01 N5/00. Process for N-alkyl anilines synthesis/G. Esipov, A. Yazlovitskiy, N. Onischenko, 1. Kishkovskaya (USSR).—No 2484138/23-04; filed 10 May 1977; published 5 Jun. 1979. Bul. No No 21-3c.].

Since it is stated that the process does not enable to shift this reaction toward monoalkylamines, it is not acceptable for us. In case of its application to produce N-methyl-para-anisidine, the situation becomes even worse. Besides, the catalyst used in the reaction is acidic that may promote hydrolysis of the para-anisidine etheric group.

The process is known for synthesis of aniline and N-methylaniline from nitrobenzene, methanol and hydrogen in the gaseous phase on the heterogeneous copper-chromium industrial catalyst of NTK series resulting in aniline and N-methylaniline. N-methylaniline and aniline output is 95% expressed as nitrobenzene [Pat. 2135460, Russian Federation, IPC$^6$ C07C209/36, C07C209/16, C07C211/46, C07C211/48. Co-production of aniline and N-methylaniline/Yu. Batrin, Yu. Nikolaev et al.—No 97120738/04, filed 16 Dec. 1997, published 27 Aug. 1999].

This method is interesting for us and allows application of cheaper raw materials to produce target product. However, high thermal load in any catalyst layer resulting in catalyst destruction is significant disadvantage of the process thus considerably narrowing the range of catalysts, which may be used for the process. Besides, as applied to our task, high temperature may promote hydrolysis of etheric group in para-anisidine and N-methyl-para-anisidine. The above-mentioned shortages are common for all synthesis processes, in which aromatic nitrocompounds are used as raw material. Increased content of tertiary amine impurity is also a common shortage, especially during the initial contacting period.

Enhanced process is known to produce N-methyl substituted aromatic amines by reduction of corresponding nitrocompounds with methanol in the vapor phase at increased temperature. The process is carried in presence of industrial copper-containing catalyst Virgon, C-40 or NTK-10-7F modified by nickel, palladium or platinum in amount of 0.3-10 wt. %. The process is usually carried out at a temperature 200-260° C., atmospheric pressure and flow rate 0.5-2.5 h$^{-1}$ of the liquid initial mixture containing methanol and aromatic nitrocompounds while keeping the ratio between methanol and aromatic nitrocompound in the initial mixture between 1:1 and 5:1. Total output of aromatic amines is up to 99.5%, product capacity is up to 0.4-1.3 (g/g)*h. Depending on the ratio of used reagents, the process allows changing the ratio of N-methyl substituted and non-substituted aromatic amines obtained during the reaction [Pat. 2207335, Russian Federation, IPC$^7$C07C211/48, C07C211/46, C07C209/36. Synthesis process for aromatic amines by reduction of corresponding nitro compounds/V. Vinokurov, V. Stytsenko et al.—No 2001111547/04, filed 28 Apr. 2001, published 27 Jun. 2003].

Application of expensive catalyst modified by platinum metals is another disadvantage of this method apart from ones listed in the previous process. Application of such catalyst may be justified only by its increased service life, which is not stated in the patent.

Enhanced process is known for N-methylaniline synthesis by alkylation of nitrobenzene or its mixture with methanol using formaldehyde on copper-containing catalysts at a temperature 220-260° C. Molar ratio between nitrobenzene and alkylating agent is usually 1:(2.5-6.0); and optimum ratio between formaldehyde and methanol in alkylating agent is 1:1 on oxidic copper-containing catalysts promoted by manganese, chromium, iron and cobalt oxides with aluminium oxide as a carrier. At the same time, formaldehyde may be used as its aqueous solution in hydrogen presence at molar ratio nitrobenzene:hydrogen=1:(3.0-6.0). Proposed process makes possible to simplify and cheapen technology and to decrease energy consumption at nitrobenzene conversion degree up to 100% and target product output (N-methylaniline) 80-88%. [Pat. 2240308, Russian Federation, IPC C07C211/48, C07C209/26. Synthesis process for N-methylaniline/B. Gorbunov, S. Slepov et al.—No 2003106495/04, filed 7 Mar. 2003, published 20 Nov. 2004].

Application of formaldehyde aqueous solution is the process significant disadvantage resulting in the need to dispose large water amount that inevitably makes production process expensive as well as formaldehyde tendency to polymerization.

The process is known for N-methylaniline synthesis from nitrobenzene, methanol and hydrogen in gaseous phase on copper-containing catalyst containing zinc and chromium compounds.

In this case, process is carried out during two phases in two series-connected contact reactors. Nitrobenzene and methanol are fed in each reactor as a mixture or separately: nitrobenzene is fed into the first reactor while methanol—into the second one. Catalyst is loaded into the first reactor layer-by-layer thus forming the "frontal layer", which temperature should not exceed 350° C., and which volume is 10-50% of the total catalyst volume. Catalyst used in the first reactor has the following composition: copper oxide—37-40 wt. %, chromium oxide—18-20 wt. %, zinc oxide—20 wt. %, aluminium oxide—the rest. In both reactors, one may use copper-containing catalyst with the following composition: copper oxide—21.4-26.4 wt. %, chromium oxide—3.4-5.8 wt. %, aluminium oxide—3.3-22.3 wt. %; copper and zinc chromite (with empiric formula $Zn_xCu_yCr_2O_4$, where: x=0.8-10; y=0.4-0.9)–54.5-71.9 wt. % [Pat. 2263107, Russian Federation IPC$^7$ C07C211/48, C07C209/26. Two-stage method for N-methylaniline synthesis/B. Gorbunov, A. Utrobin et al.—No 2003131054/04, filed 22 Oct. 2003, published 27 Oct. 2005]. The main shortage of this process is the complexity while harmonizing operation of two reactors with different performance, which changes during operation.

The process is known for N-methylaniline synthesis by reductive alkylation of nitrobenzene or its mixture with aniline. Alkylation is carried out in the gaseous phase using methanol on oxidic copper-chromium catalyst.

During the synthesis, reductive alkylation takes place in the mixture of hydrogen and carbon dioxide at a molar ratio approx. 3:1, which is obtained by methanol vapor-phase condensation with water. The mixture containing hydrogen and carbon dioxide, which is prepared in a separate contact reactor, is supplied to reductive alkylation. [Pat. 2275353, Russian Federation, IPC C07C209/36, C07C211/48. Process for N-methylaniline synthesis/B. Gorbunov, S. Slepov et al.—No 2004107764/04, filed 15 Mar. 2004, published 27 Apr. 2006]. The process shortage is sophistication of the catalytic plant without obvious positive results. Catalyst service life before unloading is unknown.

Improved process is known for N-methylaniline synthesis by reductive N-alkylation of aniline. Proposed process is implemented at increased temperature, usually at 180-280° C., on copper-containing catalysts with copper content 9-60 wt. % in equivalent of copper oxide. The process includes catalyst reduction at 180-200° C. and further isolation of the target product from catalyst using rectification. The process is carried out in spent gases instead of hydrogen; these gases are also used for catalyst reduction. [Pat. 2270187, Russian Federation, IPC C07C209/36, C07C211/48. Method for N-methylaniline synthesis/V. Golovachev, V. Dogadaev.—No 2004111480/04, filed 14 Apr. 2004, published 20 Feb. 2006]. As in the previous process, catalyst service life is unknown.

The process is known for liquid-phase catalytic synthesis of alkylated aniline.

Aniline is alkylated with formaline at a ratio aniline:formaline=1.6/1.1 in the presence of hydrogen on non-movable palladium catalyst in ethyl or methyl alcohol at a temperature 55-65° C. and pressure 0.2-0.4 MPa. The process is carried out in the cylindrical reactor fastened on the rocking device with rocking frequency 120-160 min$^{-1}$. Porous packaged cellular palladium catalyst is put into the middle part of the reactor; its active layer is modified with palladium nano-particles; it has porosity 70-95% and palladium content 1.8-3.7%. Hydrogen is fed through the nipple located on the reactor cover. This method allows to decrease energy consumption and the by-product quantity. [Pat. 2270831, Russian Federation, IPC C07C211/48, C07C209/26, B01J23/44, B01J35/04. Process for liquid-phase catalytic alkylation of aniline/A. Revina, A. Kozlov et al.—No 2004133550/04, filed 18 Nov. 2004, published 27 Feb. 2006]. As the process disadvantage, one should note low selectivity by monomethylaniline. In particular, the process is carried out with lack of formaline at a ratio aniline:formaline=1.6:1.1 due to this reason and try to increase selectivity in any way. Catalyst is too expensive; and its price makes this process completely inappropriate for industrial application.

The process is known for the liquid-phase catalytic alkylation of aromatic amines. It comprises alkylation of aromatic amines in the presence of hydrogen and low alcohols at a temperature 50-70° C. on a heterogeneous catalyst. The process distinctive feature is the amine alkylation with formaline in the reactor with the reaction zone filled with packaged high-porous (porosity at least 70-95%) cellular carrier based on aluminium oxide and active component—palladium with weight content 1.3-2%.

The process offers to produce mainly monomethylniline, reduce palladium content in the catalyst as well as the reaction pressure and flow resistance of the catalyst layer. [Pat. 2285691, Russian Federation IPC C07C211/48, C07C209/26, B01J21/04, B01J23/44, B01J35/04. Process for liquid-phase catalytic alkylation of aromatic amines/A. Kozlov, V. Grunskiy, A. Bespalov.—No 2005112854/04, filed 28 Apr. 2005, published 20 Oct. 2006]. The process features with the disadvantages typical for the previous one.

Improved process is known to produce aniline and N-methylaniline by the gaseous-phase catalytic reduction of nitrobenzene using aqueous methanol or formaldehyde solutions. During the synthesis of aniline and N-methylaniline, reduction is carried out with aqueous methanol solution 60-80 wt. % at a molar ratio nitrobenzene:methanol=1:1.1-3.5. [Pat. 2259350, Russian Federation IPC$^7$ C07C211/48, C07C211/46, C07C209/26, C07C209/36. Process for synthesis of aniline and/or N-methylaniline and catalyst for this process/B. Gorbunov, S. Slepov.—No 2003121732/04, filed 14 Jul. 2003, published 27 Feb. 2005]. The process disadvantage is the large additional amount of contaminated water directed to treatment, which considerably worsen economic parameters of the process.

The process is known for N-methylaniline synthesis by the catalytic nitrobenzene hydrogenation with hydrogen in the presence of methanol on the catalyst containing copper, chromium and aluminium.

The process is carried out sequentially in two reaction zones at a temperature 160-200° C. in the first zone to complete nitrobenzene conversion and at 210-240° C. in the second zone until aniline conversion degree at least 93% at a molar ratio nitrobenzene:methanol:hydrogen=1:(2-4):(4-10). The process permits to produce the target product with the output exceeding 92%. [Pat. 2223258, Russian Federation IPC$^7$ C07C211/48, C07C209/36. Process for N-methylaniline synthesis/Yu. Batrin, M. Starovoitov et al.—No 2003100842/04, filed 15 Jan. 2003, published 10 Feb. 2004].

This patent does not describe how it is possible to maintain temperature 160-200° C. in the first zone, where the frontal layer effect appears. Maintaining this temperature is possible only at very low nitrobenzene load into the reactor, at low reactor performance, which does not have practical importance.

Two-stage process is known for N-methylaniline synthesis by the vapor-phase catalytic N-alkylation of aniline with methanol:aniline and methanol are fed to the first stage at a molar ratio 1:2; process is carried out at a temperature 230-260° C. and contact load 0.7-0.9 h$^{-1}$ until the aniline conversion degree into N-methylaniline becomes equal 85-95%. Catalysate is supplied to the second stage (additional alkylation) at 220-240° C. until aniline conversion degree exceeds 98%. Catalyst used at both stages is based on copper oxides promoted with manganese, iron, chromium, nickel, cobalt oxides. There are following technical results of the process: catalysate with N-methylaniline weight percent exceeding 98% in the oil fraction enabling to isolate the final product using the simplified rectification scheme; power consumption decrease; longer service life of the catalyst. [Pat. 2232749, Russian Federation IPC$^7$ C07C211/48, C07C209/18. Two-stage process for N-methylaniline synthesis/N. Mitin, S. Slepov et al.—No 2002121792/04, filed 7 Aug. 2002, published 20 Jul. 2004].

This patent, as the previous one, is intended to solve the technical task on selective synthesis of secondary amine with complete conversion of raw materials. The task is solved in the same way by dividing reactor into two zones; moreover, temperature conditions are almost the same in both patents. As per the first zone, they are completely opposite both by temperature and loading. Generally, this problem is solved in any considered process both patents using one or another way (selection of catalysts, operation modes, etc); and, probably, zoned approach is also possible.

The process is known for synthesis of N-alkylanilines from aniline derivatives and alcohol with common formula

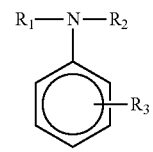

where:
R$_1$ is one radical selected from H, CH$_3$, C$_2$H$_5$,
R$_2$ is one radical selected from H, CH$_3$, C$_2$H$_5$,
R$_3$ is H ion or CH$_3$, C$_2$H$_5$ radical. Process is carried out on the catalyst of NTK series at a temperature 230-270° C. and is characterized in that the necessary amount of nitrobenzene or its derivative is added to the reaction mixture in order to maintain the necessary reactor temperature Nitrobenzene derivative corresponds to the alkylaniline produced and has the common formula:

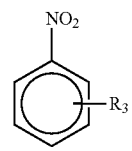

where R$_3$ is H-ion or CH$_3$, C$_2$H$_5$ radical. [Application 2002130524, Russian Federation, IPC' C07C211/48, C07C209/60. Process for N-alkylanilines synthesis/T. Rudakova, A. Kachegin et al.—No 2002130524/04, filed 14 Nov. 2002, published 27 Jan. 2005].

Using this method, it is possible to maintain temperature only in the catalyst frontal layer rather than the whole reactor.

The process is known for N-methylaniline synthesis from nitrobenzene and methanol on the NTK-series catalyst at atmospheric pressure and 230-270° C. The process is characterized in that methanol is used as a hydrogen source for nitrobenzene reduction at a molar ratio nitrobenzene:methanol equal to 1:(4-10). [Application 2003100063, Russian Federation, IPC$^7$ C07C211/48, C07C209/18. Process for N-methylaniline synthesis/N. Belyakov, N. Vavilov et al.—No 2003100063/04, filed 9 Jan. 2003, published 10 Jul. 2004].

Excessive alcohol becomes a source of hydrogen in all processes of arylamine alkylation with alcohols without application of gaseous hydrogen.

The process is known for N-methylaniline synthesis from nitrobenzene, methanol and hydrogen in gaseous phase at the heat carrier temperature 170-300° C. and catalyst temperature 350-450° C.

The process is carried out in a two-stage reactor by catalytic reduction of nitrobenzene with further aniline alkylation with methanol without aniline isolation as final product; alkylation is performed on copper oxide catalyst containing zinc and chromium compounds. The distinctive feature of the method is that the process is performed in the two-stage reactor, which second stage is a cavity adiabatic contact reactor filled with grained catalyst. [Application 2004104170, Russian Federation, IPC$^7$ C07C211/48. Process for N-methylaniline synthesis/Yu. Nikolaev, N. Belyakov.—No 2004104170/04, filed 16 Feb. 2004, published 27 Jul. 2005]. The method is featured by the following disadvantages: very high temperature in the catalyst frontal layer will inevitably result in destruction of etheric group in para-nitroanisole, para-anisidine and N-methyl-para-anisidine; the frontal layer catalyst is of acidic type thus enhancing destruction process.

Catalytic production process is known for secondary cyclic amines by interaction of corresponding primary cyclic amine with alcohols having low boiling point. This method consists of reactions in the presence of catalytic mixture containing metallic copper, aluminium oxide and metal oxides; that's why, cyclic amines may be produced cost-effectively. This invention is offered to produce N-methylaniline from aniline and methanol using alcohol stoichiometric excess, which significantly increases aniline conversion into N-methylaniline and completely suppresses formation of N,N-dimethylaniline.

As a result, comparatively pure product is obtained by using distillation intended to remove non-reacted alcohol and water formed during the reaction. Catalyst operation life between reactivations is 250 hours. [U.S. Pat. No. 2,580,284, USA. Production of secondary aromatic amines/—Thomas J. Dea'h et al.—published 25 Dec. 1951]. Catalyst contains a plenty of acidic aluminium oxide; that's why, etheric group hydrolysis is very probable while using this process for production of N-methyl-para-anisidine.

The process is known to produce secondary alkyl-aromatic amines by direct alkylation of primary aromatic amines with primary aliphatic alcohols. Secondary amine purity is achieved by distillation or crystallization from corresponding solution. Final product output achieves 70-90% while using normal aliphatic alcohols and 40-50% while using branched aliphatic alcohols. Raney nickel is used as the alkylation catalyst. [U.S. Pat. No. 2,813,124, USA. Preparation of secondary aromatic amines/Rip G Rice—published 12 Nov. 1957]. Low secondary amine output is the process shortage.

Process is known for N-methylaniline synthesis by aniline reaction with methanol in the liquid phase at a temperature 150-300° C. and methanol pressure 30-200 atm.

Process is carried out on the catalyst containing copper and chromium and corresponding to the formula: Cr*Me'*Me$^2$*O, where: Me$^1$—Cu, Zn, Fe or Ni; Me$^2$—Ba, Ca, Mg or Mn, Cr. There is the following metal content in the catalyst: Cr—20-80% wt., Me$^1$—20-80% wt., Me$^2$—0-5% wt. N-methylaniline output is 95%. [U.S. Pat. No. 3,819,709, USA. Synthesis of N-methylaniline/Koichi Murai et al.—published 25 Jun. 1974]. Very high pressure during the process is its shortage.

There is a lot of papers dedicated to application of catalysts [Inventor's certificate 644526 USSR, B01J23/76, B01J21/06, C 07B 27/00. Catalyst for aromatic amine alkylation with alcohols/S. Dobrovolskiy, A. Grigorov et al. (USSR).—No 2370915/23-04; filed 9 Jun. 1976; published 30 Jan. 1979, Bul. No 4-3c.; Inventor's certificate 531319 USSR, B01J23/86. Copper-containing catalyst for aniline alkylation/S. Dobrovolskiy, R. Grizik et al. (USSR).—No 2153141/04; filed 4 Jul. 1975; published 15 May 1984, Bul. No 18-2c.; Pat. 2066563, Russian Federation, IPC6 B01J23/84, C07C211/48. Catalyst for synthesis if N-methylaniline/M. Yakushkin, Yu. Batrin et al.—No 95110306/04, filed 21 Jun. 1995, published 20 Sep. 1996.; Pat. 2066679, Russian Federation, IPC 6 C07C211/48, B01J23/86. Production process for N-methylaniline/M. Yakushkin, Yu. Batrin et al.—No 95110305/04, filed 21 Jun. 1995, published 20 Sep. 1996.; Pat. 2152382, Russian Federation, IPC$^7$ C07C211/48, C07C209/36. Production process for N-alkylanilines/M. Starovoitov, Yu. Batrin et al.—No 98122028/04, filed 7 Dec. 1998, published 10 Jul. 2000.; Pat. 2205067, Russian Federation IPC$^7$ B01J23/86, C07C211/48. Catalyst for production of N-methylaniline/N. Mitin, S. Slepov—No 2001127908/04, filed 12 Oct. 2001, published 27 May 2003.; Pat. 2274488, Russian Federation IPC C07C211/48, B01J37/02, B01J23/86. Production process for the catalyst used for N-methylaniline synthesis/S. Slepov, A. Utrobin.—No 2004130567/04, filed 18 Oct. 2004, published 20 Apr. 2006.; U.S. Pat. No. 7,468,342, USA. Catalyst and process for aromatic amine production/Yoshinori Kanamori et al.—published 23 Dec. 2008].

Let stop our examination of the ways to obtain N-alkylated aromatic amines using dehydrogenating catalysts and start considering the methods for their preparation using dehydrating catalysts.

Enhanced process is known for continuous production of N-alkylarylanilines by the reaction between aryl amines and monoatomic saturated alcohols and/or dialkyl ethers in the gaseous phase at a temperature 180-450° C. in the presence of the carrier containing phosphoric acid. Enhancement comprises application of silicic acid, which has internal surface area 50-500 m$^2$/g and contains phosphoric acid in amount of 0.1-20% wt, as well as continuous supply of phosphoric acid and/or alkyl phosphate to the catalyst during the whole process. The output of N-monoalkylanilines and N,N-dialkylanilines is 95-98%. [U.S. Pat. No. 3,957,874, USA. Continuous production of N-alkylarylamines/Toni Dockner et al.—published 18 May 1976].

The process is known for synthesis of N-alkylated aromatic amines during joint heating of aromatic amines with low aliphatic alcohols in the presence of phosphoric acid in amount 0.01-1.0 mole in conversion to equivalent nitrogen at a temperature 150-280° C.

Then, liquid phase obtained after reaction is divided into fractions with separation of N-alkylated aromatic amine. The process takes 30-130 hours depending on initial reagents. The following compounds were produced using the above described method: dimethylaniline (99.8%), N,N-dimethyl-o-tolidine (99.4%), N,N-dimethyl-o-tolidine (99.8%), N,N-dimethyl-p-tolidine (99.8%). [U.S. Pat. No. 3,969,411, USA. Process for N-alkylation of aromatic amines/Johim Schneider.—published 13 Jul. 1976].

The process is known for production of N-alkylated aromatic amines by reaction between aliphatic alcohol containing 1-6 carbon atoms and aromatic amine having 1 hydrogen atom bonded with nitrogen in the amino group. Reaction takes place in the vapor phase at a temperature 250-450° C. in the presence of the catalyst comprising aluminium oxide treated by hydrosilicofluoric acid. Monoalkyl amine output is about 80% at the conversion rate of initial amines about 60%. At the same time, tertiary amines are formed with the output about 10%. Aromatic amines, which may be alkylated according to the conditions described in this patent, are aniline, o-, m- and p-toluidine, o-, m- and p-xylidine, o-, m- and p-anisidine. Using this process, the following compounds are produced: monoethyl-m-toluidine (48-92%) and diethyl-m-toluidine (8-22%). The possibility to use relatively low temperature for the reaction is the process advantage while high price of aldehydes and ketones is the shortage as well as their tendency for polymerization.

Patent description does not contain such important process parameters as the catalyst loading by the reaction mixture and catalyst service life. However, there is no need in these data since even the catalysate composition shows that the process is of little use for industrial application due to the difficulties connected with catalysate division into components. [Pat. 4029707, CHIA. Preparation of n-alkylated aromatic amines/Charles W. Hargis.—published 14 Jun. 1977].

The process is known for synthesis of N-alkylated aromatic amines by the reaction between aliphatic or cycloaliphatic alcohols and aromatic amines at increased temperature and pressure in the presence of catalyst and phosphorus oxyhalides. Alkylation temperature is 200-400° C., pressure is 3-20 MPa. Final product output is 43-46% for N-alkylanilines and 3-8% for N,N-dialkylanilines; the rest is non-reacted aromatic amine. [U.S. Pat. No. 4,268,458, USA. Process for production of N-alkylated aromatic amines/Werner Schulte-Hrmann, Heinz Hemmerich.—published 19 May 1981].

The process is known for synthesis of para-substituted aromatic amines by performing para-replacement reaction of aromatic carbamino acid ether with aromatic amine in the presence of aliphatic and cycloaliphatic alcohols.

Reaction is carried out at 100-260° C. and decreased or atmospheric pressure. The following compounds were produced as a result of para-substitution according to the described process: 4-t-pentylaniline (83% from the predicted value) and 4-t-butylaniline (80% from the predicted value). [U.S. Pat. No. 4,359,584, USA. Production of para-substituted aromatic amines/Franz Merger, Gerhard Nestler—published 16 Nov. 1982].

The process is known for synthesis of N-alkyl- and N,N-dialkylaniline by alkylation of aniline with alcohols, preferably with methanol and ethanol, in the presence of ZSM-5 catalyst. Application of modified ZSM-5 catalyst promotes the selectivity increase to perform N-alkylation. At the same time, formation is suppressed for undesirable by-products like toluidines. Molar ratio of silicon oxide and aluminium oxide on the catalyst is from 20:1 to 700:1; preferable ratio is from 30:1 to 200:1. Aluminosilicate may be modified by ions of alkali, alkali-earth and transition metals, preferably cesium, potassium, magnesium and iron. Reagents contact in the catalyst presence at a temperature 300-500° C., pressure 1-3 atm and a molar ratio of the alcohol and aniline 1-6. Feed rate is 0.2-4 g of raw materials per gram of the catalyst per hour. As a result, N-methylaniline (51-89%) and N,N-dimethylaniline (9-40%) are produced depending on the type of applied catalyst.
[U.S. Pat. No. 4,801,752, USA. Preparation of N-alkyl and N,N-dialkylaniline/Po Y. Chen et al.—published 31 Jan. 1989].

The issues were studied concerning aniline alkylation by methanol in the vapor phase on ZSM-5 zeolites. It was revealed that selectivity by C- and N-alkylation is depended directly on acid-base properties of the catalyst; at the same time, its activity and selectivity towards N-alkylation increases at the increase of the zeolite base strength. Service life is not indicated for applied catalysts. [Chen P. Y., Chu H. Y., Chuang T. K., Chem. Abst, v. 107, 1987]. This conclusion was confirmed during N-alkylation of o-toluidine with methanol on the acidic H-β-zeolite. Thus, 2,4-xylidine (69%) and 2,6-xylidine (up to 4%) were formed mainly during this reaction using this catalyst at a temperature 400° C., i.e. C-alkylation took place mainly. Catalyst service life was not indicated. [Anand R., Maheswari R., Journal of molecular catalysis A: Chemical, 192, p. 253, 2003]. Comparison of the results obtained on catalysts with phosphoric acid and zeolites reveals that they are very similar for aniline methylation. At the same time, reaction is better in the presence of zeolite for the aniline ethylation.

The process is known for N-alkylation of anilines by reaction of anilines with low alcohols or dialkyl ethers in vapor phase at increased temperature in the presence of zeolite pentasil-type catalysts containing protons and having molar ratio $SiO_2/Al_2O_3$ at least 60.

The temperature, at which reaction takes place, is 220-370° C. The following compounds were produced: N-monomethylaniline (1-62%), N,N-dimethylaniline (5-93%), N-ethylaniline (20-52%), N,N-diethylaniline (4-6%), N-ethyl-m-toluidine (50-52%) and N,N-diethyl-m-toluidine (5-6%) depending on the type of used catalyst and a molar ratio alcohol:aniline. Operation life of the catalyst used was not indicated. [U.S. Pat. No. 5,068,434, USA. Process for the preparation of N-alkylated anilines/Gunter Klug et al.—published 26 Nov. 1991].

Gas-phase process is known including interaction of primary aromatic amine (aniline or substituted aniline) with the alcohol having 1-5 carbon atoms or ether if the N-alkylation reaction is performed using gallosilicate. Reaction takes place at a temperature 200-500° C. and atmospheric pressure. As a result of the process, N-methylaniline is produced. Selectivity of the alkylation process is 40-90% depending upon used catalyst and process conditions. [U.S. Pat. No. 5,159,115, USA. Catalytic gas-phase process for alkylation of aromatic primary amines/Peter G. Pappas et al.—published 27 Oct. 1992].

N-alkylation of aromatic amines using vapor-phase method on dehydrating catalysts has the following disadvantages:
  Low process conversion and selectivity resulting in very high content of initial amine, dialkyl amine and C-alkyl amine in the catalyst thus complicating isolation of target monoalkyl amine by rectification;
  High process temperature resulting in problems with heat carriers and reduces catalyst operation life due to its gumming;
  Low catalyst operation life resulting in such negative aftereffects as the productive time decrease, decrease of the process automation degree, increase of capital expenditures for equipment and working hours.

Based on the above-mentioned data, it is not advised to perform N-alkylation using dehydrating catalysts for the N-methyl-para-anisidine production.

While analyzing literature and patent sources concerning production of N-alkyl substituted aromatic amines, we were not able to find the papers, in which the process was described for the synthesis of N-methyl-para-anisidine from para-anisidine or para-nitroanisole, and which contains process parameters. Certain papers point out the possibility of methylation, including para-anisidine; however, no examples were given. Besides, in certain cases it is economically inadvisable to synthesize N-methyl-para-anisidine using described processes; or described methods do not relate to the essence of our invention. We were also able to find the USSR inventor's certificate, in which the possibility is examined to alkylate para-anisidine with aliphatic alcohols C5-C9 (not with methanol) in liquid phase on Renay nickel during boiling with reverse condenser.

In this connection this study does not relate to the essence of our invention.

A plenty of works dedicated to alkylation of aromatic amines shows that this process is complicated enough; and selection of raw materials, alkylating agents, selective, efficient and stable catalyst, processing conditions is the individual task for each matter.

The object of the invention is to provide synthesis of N-methyl-para-anisidine with purity at least 98% and high output that allow to arrange highly-profitable heavy-tonnage production process.

The most close to the proposed way for synthesis of N-methyl-para-anisidine is the process [RF patent 2135460] for combined synthesis of aniline and N-methylaniline from nitrobenzene and methanol in the vapor phase on NTK-4 heterogeneous copper-chromium catalyst. We took the process described in this patent as a prototype per totality of common features. According to this method, aniline or N-methylaniline is produced mainly depending upon the ratio methanol:nitrobenzene. This method features by versatility and simple equipment as well as the absence of high pressure. This process was not used to produce N-methyl-para-anisidine.

Technical result is achieved by N-alkylation of para-nitroanisole or para-anisidine with methanol in the vapor phase at atmospheric pressure and 180-260° C. using dehydrogenating catalyst Raney nickel and copper-chromium catalyst modified with oxides of barium, calcium, zinc, etc. including NTK-series and BASF industrial catalysts. In particular, catalysts with the following composition were used:

CuO—55%; ZnO—10.5%; $Cr_2O_3$—13.5%; $Al_2O_3$—the rest;

CuO—25%; ZnO—25%; CaO—5%; $Al_2O_3$—the rest;

CuO—25-45%; BaO—2-10%; $TiO_3$—15-35%; $Cr_2O_3$—the rest;

CuO—35-45%; ZnO—25-35%; NiO—3-8%; $Al_2O_3$—the rest;

CuO—12-19%; MnO—2-3%; $Cr_2O_3$—1.0-1.4%; $Fe_2O_3$—1.0-1.4%; $Co_3O_4$—0.5-0.8%;

$Al_2O_3$—the rest;

Raney nickel;

BASF Cu-E403TR catalyst with the following composition: copper chromite—67-71%, copper—11-15%, copper oxide—8-21%, graphite—0-4%, chromium (3+) oxide—0-3%;

BASF Cu-0203T 1/8 catalyst with the following composition: copper oxide—75-100%, chromium (3+) oxide—0.1-1%;

BASF Cu-E406TR catalyst with the following composition: Cu-36%, Cr-31%, Ba-6%.

To increase the process selectivity concerning N-methyl-para-anisidine, it is proposed to introduce triethylamine into the reaction mixture, which inhibits formation of N,N-dinethyl-para-anisidine impurity, in molar ratio triethylamine:initial nitrocompound=(0.05-0.1):1.

At a molar ratio less than 0.05:1, almost no effect is observed; at the ratio more than 0.1:1 difficulties appear with triethylamine isolation and its return to contacting. As an alternative of the proposed solution, the N-alkylation process is carried out in the presence of triethylamine in molar ratio to para-nitroaniline and/or para-anisidine 0-0.1:1.

Conditions during the synthesis of N-methyl-para-anisidine are illustrated by the following examples:

EXAMPLE 1

100 mL of inert material (broken quartz, ceramic Raschig rings) and 100 mL of copper-chromium catalyst were loaded into the quartz tubular reactor with inner diameter 45 mm. Void volume of the reactor was again filled with inert material used for reagent evaporation. Nitrogen was passed through the reactor with a rate 200 mL/min; reactor was heated up to 200° C. Catalyst reduction was started at this temperature by supplying 5% methanol aqueous solution into the reactor; methanol feed rate was set in such a way that the temperature in the catalyst layer did not exceed 300° C. Upon completion of catalyst reduction (stopping of heat emission and temperature decrease in the catalyst layer up to 200° C.), vapor of pure methanol was transmitted through the reactor yet 1 hour. Methanol was replaced by the mixture containing 1 molar part of para-nitroanisole and 5 molar parts of methanol. This mixture was fed with a flow rate 0.125-0.2 L/h, and N-methyl-para-anisidine was synthesized. Contact gases were cooled in glass ball condenser and collected in the condensate reservoir.

Condensate was divided into aqueous and organic layer is the phase separator. Organic layer was analyzed using gas-liquid chromatography. Contact process was carried out continuously until appearance of 5% para-nitroanisole in the catalysate organic layer. Whereupon reaction mixture supply was stopped, and the plant was switched into the catalyst reactivation mode. For this purpose, water steam was fed into the catalyst; then, water steam was diluted with air gradually increasing its concentration with maintaining the temperature in the catalyst layer at most 350° C. Upon completion of reactivation process (heat stops to emit in the catalyst layer), the plant was switched into the reduction mode and then into the contact mode (above-described). Average product output was 80-85% for the contact period (200-250 hours).

Collected organic layer was separated in periodical rectification plant, intermediate products and methanol were returned to the contact. Final N-methyl-para-anisidine has concentration 98%.

EXAMPLE 2

As in example 1; however, par-anisidine was used instead of para-nitroanisole. Load of the reaction mixture on catalyst was 30-40 mL/h. Catalysate in oil layer contains para-anisidine 0-10%, N-methyl-para-anisidine 88-95% and N,N-dimethyl-para-anisidine 2-5%. N-methyl-para-anisidine was obtained with output 83-88%.

EXAMPLE 3

As in example 1; but the process was carried out in the nitrogen stream.

EXAMPLE 4

As in example 1, but the process was carried out in the hydrogen stream at a molar ratio para-nitroanisole:hydrogen=1:(3-5).

EXAMPLE 5

As in example 2, but the process was carried out in the nitrogen stream.

EXAMPLE 6

As in example 2, however, the process was carried out in the hydrogen stream at the ratio: para-anisidine—1 molar part, methanol—2 molar parts, hydrogen—3-5 molar parts.

EXAMPLE 7

As in examples 1, 3, 4; however, in the presence of triethylamine at a molar ratio to para-anisole 0.1:1. N-methyl-para-anisidine was produced with output up to 92%.

EXAMPLE 8

As in examples 2, 5, 6; however, in the presence of triethylamine at a molar ratio to para-anisidine 0.1:1. N-methyl-para-anisidine was produced with output up to 95%.

Examples No 1, 2, 3, 4, 5, 6, 7, 8 were carried out using catalysts with the following composition:

CuO—55%; ZnO—10.5%; $Cr_2O_3$—13.5%; $Al_2O_3$—the rest;

CuO—25%; ZnO—25%; CaO—5%; $Al_2O_3$—the rest;

CuO—25-45%; BaO—2-10%; $TiO_3$—15-35%; $Cr_2O_3$—the rest;

CuO—35-45%; ZnO—25-35%; NiO—3-8%; $Al_2O_3$—the rest;

CuO—12-19%; MnO—2-3%; $Cr_2O_3$—1.0-1.4%; $Fe_2O_3$—1.0-1.4%; $Co_3O_4$—0.5-0.8%; $Al_2O_3$—the rest;

Raney Nickel Catalyst;

BASF Cu-E403TR catalyst with the following composition: copper chromite—67-71%, copper—11-15%, copper oxide—8-21%, graphite—0-4%, chromium (3+) oxide—0-3%;

BASF Cu-0203T 1/8 catalyst with the composition: copper oxide—75-100%, chromium (3+) oxide—0.1-1%;

Similar results are obtained. Catalyst operation resource is 2,000 hours.

The invention claimed is:

1. A process for producing N-methyl-para-anisidine, the process comprising the steps of:
   a) providing para-anisidine, methanol and a copper-chromium dehydration catalyst modified with one or more of oxides of barium, oxides of zinc, oxides of aluminum, oxides of titanium, oxides of iron, oxides of calcium, oxides of magnesium, oxides of nickel and oxides of cobalt;
   b) causing N-alkylation of the para-anisidine with the methanol in the vapor phase over the dehydration catalyst at a temperature of 180 to 260° C. and at atmospheric pressure; and
   c) isolating the resultant N-methyl-para-anisidine by rectification.

2. The process of claim 1, wherein the N-alkylation step is carried out in the presence of nitrogen.

3. The process of claim 1, wherein the N-alkylation step is carried out in the presence of hydrogen.

4. The process of claim 1, wherein the catalyst comprises 55% by weight CuO, 10.5% by weight ZnO, 13.5% by weight $Cr_2O_3$, balance $Al_2O_3$.

5. The process of claim 1, wherein the catalyst comprises 25% by weight CuO, 25% by weight ZnO, 5% by weight CaO, balance $Al_2O_3$.

6. The process of claim 1, wherein the catalyst comprises 25-45% by weight CuO, 2-10% by weight BaO, 15-35% by weight $TiO_3$, balance $Cr_2O_3$.

7. The process of claim 1, wherein the catalyst comprises 35-45% by weight CuO, 25-35% by weight ZnO, 3-8% by weight NiO, balance $Al_2O_3$.

8. The process of claim 1, wherein the catalyst comprises 12-19% by weight CuO, 2-3% by weight MnO, 1.0-1.4% by weight $Cr_2O_3$, 1.0-1.4% by weight $Fe_2O_3$, 0.5-0.8% by weight $Co_3O_4$, balance $Al_2O_3$.

9. The process of claim 1, wherein the catalyst further comprises Raney nickel.

10. The process of claim 1, wherein the catalyst comprise 75-100% by weight copper oxide, 0.1-1% by weight chromium ($3^+$) oxide.

11. The process of claim 1, wherein the catalyst comprises 36% by weight Cu, 31% by weight Cr, and 6% by weight Ba.

12. The process of claim 1, wherein the N-alkylation step is carried out in the presence of triethylamine and the molar ratio of triethylamine to para-anisidine is 0.05-0.1:1.

* * * * *